April 9, 1946. W. E. LAMMERTS Plant Pat. 676
ROSE PLANT
Filed Jan. 23, 1945
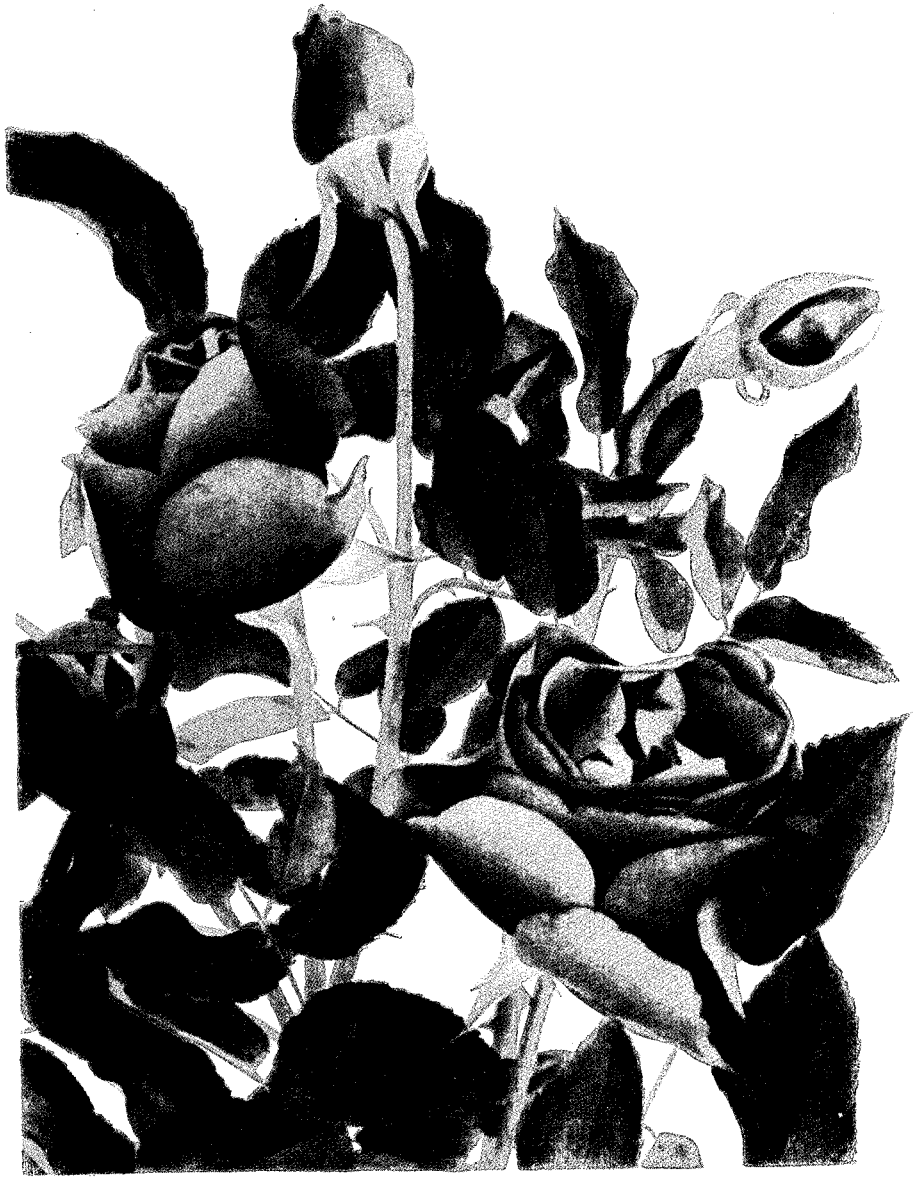
Inventor
W. E. Lammerts
By Robert Robb
His attorneys Patented Apr. 9, 1946

UNITED STATES PATENT OFFICE

676

ROSE PLANT

Walter E. Lammerts, West Los Angeles, Calif., assignor to Armstrong Nurseries, Inc., San Bernardino, Calif., a corporation of California Application January 23, 1945, Serial No. 574,105

1 Claim. (Cl. 47—61)

The present invention relates to a new and distinct variety of rose plant, having as its primary feature of distinction, the unique dark red color of its blossoms, and their more desirable fading reaction, as compared with other known varieties of red roses, when grown under comparable conditions.

This new variety is the result of inbreeding of the well known variety "Crimson Glory" (Pl. Pat. #105) and it is similar thereto insofar as habit and vigor of growth are concerned, but differing therefrom in many respects, as more specifically will appear hereinafter. Among the more important of these specific distinctions may be mentioned the foliage which in the new variety is somewhat more plentiful, more narrow, and slightly more resistant to mildew.

Not only is this new rose characterized as to novelty by its new shade of color in dark red roses, but its bud and open flower are of a new shape among red roses, the bud being more urn-shaped than ovoid and the open flower flat with strongly reflexed tips.

As to the fading reaction, this new rose is believed to be more desirable than any red rose now available in that it attains less blue (as this term is commonly used in connection with red roses) than any other red variety now available in commerce.

Asexual reproduction of this new variety shows the foregoing characteristics come true to form and are established.

The drawing shows specimens of this variety in various stages of development.

The following is a detailed description of this new variety, the color terminology being in accord with the Robert F. Wilson Horticultural Colour Chart, except where otherwise designated as taken from Ridgway's Color Standard:

Type: Bush; seedling; for cut flowers and garden decoration.

Class: Hybrid tea.

Breeding: Seedling.

*Seed parent.*—"Crimson Glory."

*Pollen parent.*—"Crimson Glory."

Propagation: Holds its distinguishing characteristics through succeeding propagations by budding, which is the only method tried up to the present.

*Flower*

Locality where grown: Ontario, California.

Flowers borne: Singly to two, three, four or five to stem; in irregular flat to rounded cluster; on normal medium long stems.

Quantity of bloom: Free; outdoors.

Continuity: Continuous.

Fragrance: Moderate; spicy.

Bud:

*Pedicel.*—Medium length; medium heavy; erect; almost smooth; numerous gland-tipped cilia. *Color*—near Parrot Green, Plate VI (Ridgway). Side exposed to sun, tinted with near Deep Vinaceous Gray, Plate L (Ridgway).

*Before calyx breaks.*—*Size*—medium. *Form*—ovoid, without a conspicuous neck; with foliaceous appendages, tomentum, gland-tipped cilia, glandular bloom, on the surface of the bud; with slender, much-cut foliaceous parts extending beyond the tip of the bud equal to ¼ or more of its length.

*As calyx breaks.*—*Color*—near Chrysanthemum Crimson, Plate 824. *Inner surface*—with fine, woolly tomentum. Usually three sepals with stipitate glands on both margins and two sepals with woolly tomentum on both margins. Sometimes alternate sepals cover one margin of a particular sepal, causing this sepal to have one margin with stipitate glands and one margin with woolly tomentum only.

*As first petal opens.*—*Size*—medium. *Form*—ovoid. *Color*—outside—near Chrysanthemum Crimson, Plate 824. Inside—near Cardinal Red, Plate 822. *Opening*—opens up well.

Bloom:

*Size.*—When fully open medium; 3½ inches to 4½ inches.

*Petalage.*—Semi-double to double, but stamens not hidden; 14 to 16 petals, arranged irregularly.

*Form.*—Open, becoming quickly recurved; petals at first loosely rolled outward; becoming later, at maturity, very loosely rolled outwardly and upwardly.

Petals: Leathery; with inside velvety and outside satiny.

*Shape.*—Outside—round; scalloped with 1 to 3, sometimes 4, notches. Intermediate—round; scalloped with 2 to 3 notches. Inside—round; scalloped with apex flat, with 2 to 3, sometimes 4, notches.

This description of a newly opened flower was made from a rose grown outdoors in the month of September, 1944, at Ontario, California:

*Color.—Outside petal*—outside surface: near Cardinal Red, Plate 822; shaded and pencilled with black; inside surface: between and varying from Cardinal Red, Plate 822, and Currant Red, Plate 821; pencilled and shaded with black. *Intermediate petal*—outside surface: near Chrysanthemum Crimson, Plate 824/2; inside surface: between and varying from Cardinal Red, Plate 822, and Currant Red, Plate 821; pencilled and shaded with black. *Inner petal*—outside surface: near Chrysanthemum Crimson, Plate 824/1; inside surface: beween and varying from Cardinal Red, Plate 822, and Currant Red, Plate 821; pencilled and shaded with black, often with pencilling of white from base of petal toward apex.

This description was made from a rose that was open for three days outdoors in the month of September, 1944, at Ontario, California:

*Color.—Outside petal*—outside surface: near Cardinal Red, Plate 822, shaded and pencilled with black; inside surface—near Cardinal Red, Plate 822/1, pencilled and shaded with black. *Inside petal*—outside surface: near Cardinal Red, Plate 822; shaded and pencilled with black; inside surface: near Cardinal Red, Plate 822/1, pencilled and shaded with black.

*General color effect.*—Newly opened flower—between and varying from Cardinal Red, Plate 822, and Chrysanthemum Crimson, Plate 824. Three days open—between and varying from Cardinal Red, Plate 822, and Chrysanthemum Crimson, Plate 824.

*Behavior.*—Persist from one to several days; fading purple only slightly. Flower has tendency to blue more quickly in very hot weather, but only slightly compared with other red roses.

*Flower longevity.*—On bush in garden—2 to 3 days in September. Cut roses grown outdoors kept at living room temperature—3 days in September.

*Reproductive organs*

Stamens: Medium number; arranged irregularly about pistils, mixed with petaloids.

Filaments: Medium length; near Veronese Green, Plate 660/3 at base, changing toward anthers to near Rose Bengal, Plate 25/3; most with anthers.

Anthers: Medium size; all open at once approximately; near Buttercup Yellow, Plate 5/2, tinted with near Tyrian Rose, Plate 24/2.

Pollen: Moderate; white.

Pistils: Many.

Styles: Uneven; medium length; medium heavy; bunched. *Color*—near Cardinal Red, Plate 822.

Stigma: Translucent white.

Ovaries: Some protruding from calyx.

Hips: Globular, with inconspicuous neck. *Color*—near Fern Green, Plate 0862/2. Moderately smooth; glandular; walls moderately thin, fleshy.

Sepals: Permanent; moderately short; spear-shaped; curled. *Color*—inside—near Light Grape Green, Plate XLI (Ridgway); outside—base color near Light Bice Green, Plate XVII (Ridgway); blushed and pencilled with near Corinthian Red, Plate XXVII (Ridgway).

Seeds: Medium size; about 12 to 15.

*Plant*

Foliage:

*Leaves.*—5 to 7 leaflets; normally abundant; small to medium; moderately heavy; leathery.

*Leaflets.*—Ovoid with apex acute; base round; margin irregularly serrate.

*Color.—Mature*—upper surface—near Cossack Green, Plate VI (Ridgway); under surface—near Light Elm Green, Plate XVII (Ridgway). *Young*—upper surface—near Deep Dull Yellow Green, #2 Plate XXXII (Ridgway), shading toward margins to near Dark Vinaceous Gray, Plate L (Ridgway); under surface—near Light Cress Green, Plate XXXI (Ridgway), shading toward margins to near Dark Vinaceous Gray, Plate L (Ridgway).

*Rachis.* — Medium heavy. Upper side — grooved, glandular; under side—moderately smooth, having a few stipitate glands.

*Stipules.*—Medium length; medium wide; with medium long points, turning out at an angle of more than 45°, seldom recurved toward the stem.

*Disease.*—Slightly subject to mildew.

Growth:

*Habit.*—Bushy.

*Growth.*—Moderate to free.

*Canes.*—Medium to heavy.

*Main stems.*—Near Chromium Green, Plate XXXII (Ridgway). *Large prickles*—many; medium length; straight; with medium narrow base. Color—near Russet Vinaceous, Plate XXXIX (Ridgway). *Small prickles* — several. Color — near Russet Vinaceous, Plate XXXIX (Ridgway). Canes also have few stipitate glands. *Hairs*—None.

*Branches.*—Near Chromium Green, Plate XXXII (Ridgway). *Large prickles*—short; medium long; straight; with long medium narrow base. Color—near Deep Purplish Vinaceous, Plate XLIV (Ridgway). *Small prickles*—several. Color—near Deep Purplish Vinaceous, Plate XLIV (Ridgway). Branches have few stipitate glands. *Hairs*—none.

*New shoots.*—Near Turtle Green, Plate XXXII (Ridgway). Side exposed to sun slightly tinted with near Vinaceous Drab, Plate XLV (Ridgway). *Large prickles*—many; long; straight; with medium narrow base. Color — near Deep Purplish Vinaceous, Plate XLIV (Ridgway). *Small prickles*—several. Color—near Deep Purplish Vinaceous, Plate XLIV (Ridgway). *Hairs*—none.

I claim:

A new and distinct variety of rose plant, predominantly characterized as to novelty by the unique dark red color of its flowers; the urn shape of its bud; the flat-open-shape of the open flower with strongly reflex tips; the abundance of foliage, more narrow and more resistant to mildew than found in its parents; and the less tendency to bluing, as regards its fading reaction, than found in other red varieties now available in commerce, substantially as shown and described.

WALTER E. LAMMERTS.